United States Patent [19]

Fukunaga et al.

[11] Patent Number: 5,582,596
[45] Date of Patent: Dec. 10, 1996

[54] APPLICATOR FOR APPLYING A BIOCOMPATIBLE ADHESIVE

[75] Inventors: Nobuto Fukunaga, Tamana; Katsumi Kawakami; Takanori Uchida, both of Kumamoto; Yoshimitsu Ishihara, Kikuchi-gun, all of Japan

[73] Assignee: Juridical Foundation The Chemo-Sero-Therapeutic Research Institute, Kumamoto, Japan

[21] Appl. No.: 244,430

[22] PCT Filed: Sep. 24, 1993

[86] PCT No.: PCT/JP93/01364

§ 371 Date: May 26, 1994

§ 102(e) Date: May 26, 1994

[87] PCT Pub. No.: WO94/07420

PCT Pub. Date: Apr. 14, 1994

[30] Foreign Application Priority Data

Sep. 26, 1992  [JP]  Japan ..................................... 4-072992

[51] Int. Cl.⁶ .................................................. A61M 5/00
[52] U.S. Cl. ........................ 604/191; 604/82; 222/137
[58] Field of Search .......................... 604/191, 82, 272, 604/225, 8.9, 91, 35, 218, 56, 83, 85, 187, 236, 238, 249, 208, 266, 269, 94; 606/93; 222/137, 127, 142, 145.1

[56] References Cited

U.S. PATENT DOCUMENTS

| | | | |
|---|---|---|---|
| 2,112,160 | 3/1938 | Johnson | 604/191 X |
| 3,467,096 | 9/1969 | Horn | 604/191 X |
| 3,552,394 | 1/1971 | Horn | 604/191 X |
| 3,767,085 | 10/1973 | Cannon et al. | 222/82 |
| 4,329,988 | 5/1982 | Sarnoff et al. | 604/191 X |
| 4,359,049 | 11/1982 | Redl et al. | 604/82 |
| 4,610,666 | 9/1986 | Pizzino | 604/191 |
| 4,631,055 | 12/1986 | Redl et al. | 604/82 |
| 4,673,395 | 6/1987 | Phillips | 604/191 |
| 4,740,203 | 4/1988 | Hoskins et al. | 604/191 |
| 4,874,368 | 10/1989 | Miller et al. | 604/82 |
| 5,104,375 | 4/1992 | Wolf et al. | 604/56 |
| 5,116,315 | 5/1992 | Capozzi et al. | 604/82 |
| 5,226,877 | 7/1993 | Epstein | 607/35 |
| 5,322,510 | 6/1994 | Lindner et al. | 604/82 |

FOREIGN PATENT DOCUMENTS

| | | |
|---|---|---|
| 0037393 | 10/1981 | European Pat. Off. . |
| 0041022A1 | 12/1981 | European Pat. Off. . |
| 0315222A2 | 5/1984 | European Pat. Off. . |
| 0249186A1 | 12/1987 | European Pat. Off. . |
| 3417182A1 | 11/1985 | Germany . |
| WO9107197 | 5/1991 | Germany . |
| 64948 | 1/1989 | Japan . |
| WO9001959 | 3/1990 | WIPO . |

*Primary Examiner*—Randall L. Green
*Assistant Examiner*—V. Alexander
*Attorney, Agent, or Firm*—Foley & Lardner

[57] ABSTRACT

An applicator for applying a biocompatible adhesive containing human or animal protein as a principal ingredient to a surgical site of living body includes a housing to which a sterile gas is supplied, a sterile-gas supply tube connected to the housing, two adjacent sterile-gas ejecting nozzles for ejecting the sterile gas in the same direction, two adapters to which respective nozzles of syringe barrels are connected, and a pair of solution tubes, each having one end connected to the adapter and the other end protruded outwardly from the sterile gas ejection nozzle through an interior of the housing. Respective solutions supplied from the syringes via the pair of barrel adapters are ejected from the outlets of the solution tubes. The sterile gas is ejected from two sterile-gas ejection nozzles in the same direction. Consequently, the solutions are sprayed and mixed by the sterile gas, and then applied to the surgical site.

21 Claims, 9 Drawing Sheets

Fig. 2
Fig. 3
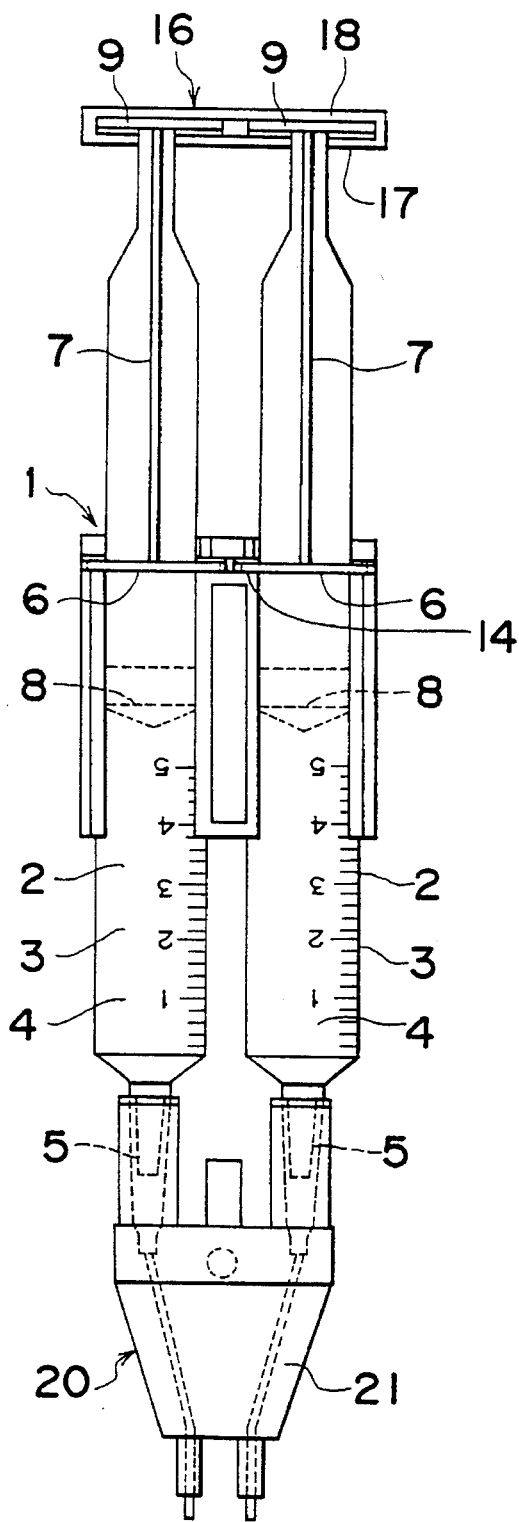
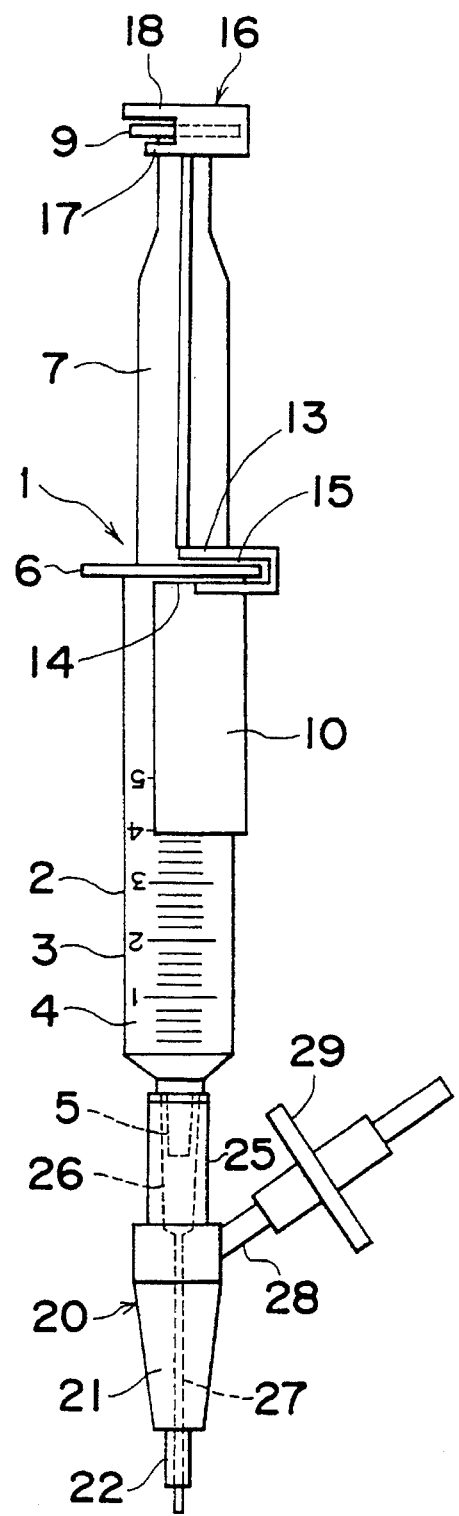

APPLICATOR FOR APPLYING A BIOCOMPATIBLE ADHESIVE

FIELD OF THE INVENTION

The present invention relates to an applicator for applying a biocompatible adhesive, containing human or animal protein as a principal ingredient, to a human or animal body, and is more particularly related to an applicator for spraying the biocompatible adhesive so as to apply it to a surgical site. This applicator is preferably used for applying the biocompatible adhesive for hemostasis of bleeding onto a resected surface of liver or lung, or a surgically sutured site of a digestive tract.

BACKGROUND OF THE INVENTION

A biocompatible adhesive mainly based on human or animal protein is generally prepared in situ by mixing a protein solution with another coagulating solution containing a coagulation factor which promotes coagulation of the protein. When applying to a surgical site the biocompatible adhesive of this kind which, for example, is a mixture of a solution containing both factor XIII and fibrinogen with another solution containing thrombin, one of two following methods are generally used in the art: to apply the first mentioned solution to the surgical site and then coating the same with the second mentioned solution, and to premix the two solutions together before the resultant mixture is applied to the surgical site by the use of a syringe.

These methods suffer from several drawbacks. For example, in the first mentioned method, surface hardening takes place before the two solutions are completely mixed together, which results in insufficient mixing and reduction of the adhesive strength. In the second mentioned method, since the hardening of the adhesive starts soon after mixing the two solutions, it is necessary to apply the adhesive to the surgical site immediately after the mixing. For this reason, this second mentioned method does not only require considerable surgical skill, but also limits its application.

To solve these problems, a method for accommodating those two solutions in syringes separately, ejecting the solutions simultaneously from the respective syringes so as to mix together and apply the resultant mixture to the surgical site, has been suggested in the Japanese Patent Laid-Open Publications No. 64-25843 and No. 64-4040, Japanese Utility Model Laid-Open Publication No. 62-62674, 62-62675, No. 62-65972, No. 62-65973, No. 62-20853, No. 1-82049, and Japanese Utility Model Publication No. 3-47609.

The applicator for applying the biocompatible adhesive described in the Japanese Utility Model Publication No. 3-47609 includes a conflux head having defined therein a pair of conveying channels for conveying two solutions, respectively, which are discharged from associated conical portions, or nozzles of the syringes. The applicator also includes a pair of sterile gas supply channels, which are so arranged in the vicinity of respective outlets of the conveying channels as to lie at a right angle to the conveying channels. Further, the sterile gas nozzles have their longitudinal axes arranged to intersect with each other at a location spaced a specific distance away from the outlets of the sterile gas nozzles.

However, this prior art applicator has the following problems. For example, since the conveying channels lies at substantially right angles to the sterile gas supply channels, that is, they do not direct to the surgical site, if the sterile gas has a low pressure, the adhesive will not be applied properly to the surgical site, or will not be sprayed in uniform density. On the other hand, if the sterile gas of a high pressure is supplied, it may possibly bring about harmful influence upon the surgical site. Also, the distance between the two outlets of the nozzles are so large that these solutions will mix together at a location spaced a distance of about 10 to 20 cm from those outlets. Therefore, the applicator is not available for application of the adhesive to the surgical site which is deep and narrow.

In addition, the sterile gas is introduced through a long tube from a sterile gas supply unit or a cylinder containing a highly pressurized sterile gas. The long tube and/or the cylinder may disturb a surgical job being performed which would cause a loss of surgical operation and a reduction in result of surgical operations.

SUMMARY OF THE INVENTION

It is therefore an object of the present invention to provide an improved applicator for applying a biologically compatible adhesive, which is effective to spray the adhesive to the surgical site even though the sterile gas is low in pressure.

Another object of the present invention is to provide an improved applicator of the type referred to above which can be easily transported and handled during the performance of an surgical operation.

A further object of the present invention is to provide an improved applicator of the type referred to above which does not make use of any long sterile gas supply tube.

To achieve the objects in accordance with the purpose of the invention, an applicator for applying a biocompatible adhesive containing human or animal protein as a principal ingredient to a surgical site of living body comprises a spray head which includes a housing to which a sterile gas is supplied; a sterile-gas supply tube connected to the housing for supplying the sterile gas thereto; a pair of adjacent sterile-gas ejecting nozzles having their longitudinal axes oriented in the same direction for guiding and ejecting the sterile gas supplied to the housing in the same direction; a pair of adapters to which respective nozzles of syringe barrels are connected; and a pair of solution tubes, each of which has one end thereof connected to the adapter and the other end thereof protruded a predetermined distance outwardly from the sterile gas ejection nozzle through an interior of the housing.

According to the applicator, respective solutions supplied from the syringes via the barrel adapters are ejected from the outlets of the solution tubes, while the sterile gas supplied to the sterile-gas supply chamber through the sterile-gas supply tubes is ejected from the sterile-gas ejection nozzles in the substantially same direction. Consequently, the solutions are sprayed and mixed by the ejection of the sterile gas.

Another embodiment of an applicator of the present invention includes a holder for holding two syringe barrels which accommodate a protein solution and a solution of coagulation factor which promotes coagulation of protein, respectively; an actuator for holding and simultaneously moving syringe plungers inserted in respective barrels; and a spray head for spraying the two solutions discharged from the respective syringe. The spray head includes a sterile-gas supply chamber, a sterile-gas supply tube connected at one end thereof to the sterile-gas chamber for feeding a sterile-gas to the sterile-gas supply chamber, a pair of adjacent sterile-gas ejection nozzles having their longitudinal axes oriented in the same direction for guiding and ejecting the sterile gas supplied the sterile-gas supply chamber in the same direction, a pair of adapters to which the respective syringe barrels are connected, and a pair of solution tubes each connected at one end thereof to the adapter through an interior of the sterile-gas supply chamber, each of said solution tubes having the opposite end protruding a predetermined distance outwardly from the sterile gas ejection nozzles.

According to this applicator, the sterile gas supplied to the sterile-gas supply chamber through the sterile-gas supply tubes are ejected from the sterile-gas ejecting nozzles in a predetermined direction. The solutions accommodated in the pair of syringes are fed to the solution tubes by biasing the actuator and pushing the respective plungers into the barrels, and then ejected from outlets of the solution tubes. As a result, the two ejected solutions are sprayed by the sterile gas ejected therearound, and mixed together.

Preferably, each of the sterile-gas ejecting nozzles further has its inner periphery surface formed with a plurality of ribs for supporting the associated solution tube in coaxial relationship therewith.

Another embodiment of the applicator of the present invention includes means for supporting a holder which holds a pair of syringe barrels; means for pushing an actuator which holds syringe plungers inserted in respective syringe barrels; a sterile gas supply source for supplying a sterile gas to a sterile-gas supplying tubes;

switching means for controlling the sterile-gas supply means and the pushing means.

Since this applicator incorporates the sterile-gas supply means, switching means and so forth, it is convenient for transportation during the surgical operation and handling. Further, since it is unnecessary to use a long tube for introducing the sterile gas from the pressurized gas source, the applicator ensures a rather safe operation. Furthermore, the solutions may be sprayed uniformly. Moreover, ejection of the sterile gas is permitted only by controlling the switching means, which results in efficient use of the sterile gas.

Further, in another embodiment, a distance between the pair of solution tubes is chosen to be about 1 to 20 mm, preferably about 1 to 5 mm.

Furthermore, in other embodiment, a length of the distal end of each solution tube which protrudes outwardly from the sterile-gas ejection nozzle is chosen to be about 0.1 to 10 mm. As a result, the solution tubes will not clog even though the spraying of the solutions are interrupted, such that turning the spraying on and off may be permitted.

Moreover, the spray head has an elongated hollow extension of an approximate length of 5 to 50 cm, the distal end thereof being formed with a pair of through-holes through which respective solution tubes extending into the extension through the rear end portion of such extension are guided so as to protrude outwardly from the extension. This permits a spraying of the solutions against a deep and/or narrow surgical site.

BRIEF DESCRIPTION OF THE DRAWINGS

FIG. 2 is a plan view of the adhesive applicator in an assembled condition;

FIG. 3 is a view similar to FIG. 2 showing the adhesive applicator as viewed from a direction with the applicator turned 90° relative to that shown in FIG. 2;

DETAILED DESCRIPTION OF THE INVENTION

Figure 1:
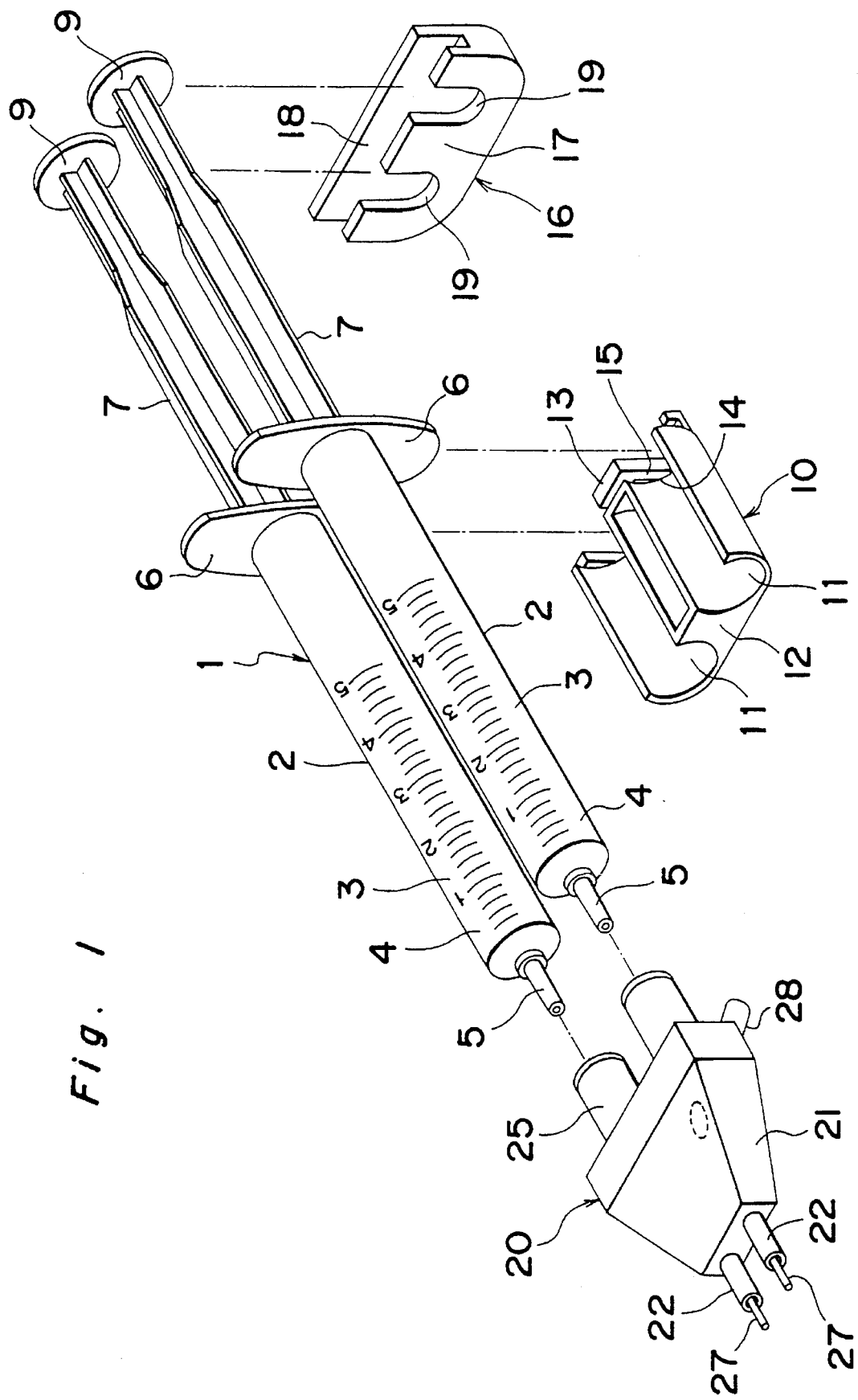
FIG. 1 is an exploded view of an adhesive applicator according to the present invention.

Referring first to FIGS. 1 to 3, there is shown an applicator for applying a biocompatible adhesive according to a first embodiment of the present invention. The applicator indicated generally by reference numeral 1 comprises a pair of syringes 2 for accommodating fibrinogen and thrombin solutions, respectively. Each syringe 2 includes a barrel 3 which comprises a cylindrical body 4, a nozzle 5 at one end of the body 4, and a terminal flange 6 projecting radially outwardly at the other end of the body 4. A plunger 7 for each syringe 2 carries at one end thereof a packing 8 which is made of elastic material such as rubber. This packing 8 has a diameter slightly larger than inner diameter of the body 4. The other end of each plunger 7 is formed integrally with a thumb yoke or finger engaging head 9. The plunger 7 is inserted into the respective barrel 3 with slidingly situated within the body 4 so that an outer peripheral surface of the packing 8 snugly contacts an inner peripheral surface of the cylindrical body 4. The barrel 3 and the plunger 7 are generally made of glass or transparent synthetic resin such as polypropylene or polycarbonate.

A syringe holder 10 for supporting these barrels 3 together is preferably made of synthetic resin such as, for example, polyethylene, polypropylene, acrylonitrile-butadiene-styrene copolymer or polycarbonate, and includes a pair of parallel concave portions 11. Each concave portion 11 has a C-shaped internal surface at a curvature complemental to that of the outer periphery of the associated cylindrical body 4. An upper end of the concave portion 11 is so designed as to have a slightly greater width than external diameter of the cylindrical body 4, which ensures the concave portion 11 to tightly retain the barrel 3 therein. Preferably, the opening width of the concave portion 11 is determined by taking both resistance for attachment of the barrel 3 and stability of the same held in the concave portion 11 into consideration. The holder 10 further comprises a stopper 13 facing but spacing a predetermined distance from one end of a connecting portion 13 defining a wall between the pair of concave portions 11, such that the flanges 6 of the barrels 3 held in the respective concave portions 11 are inserted into a gap, i.e., concave portion 15 formed between the stopper 13 and an end surface 14 confronting thereto for fixing the flanges.

An actuator 16, for simultaneously moving the syringe plungers 7 inserted in the barrel 3, is preferably made of same material as the holder 10, and comprises a front wall 17, and a rear wall 18 facing forwards, and spaced a predetermined distance from the front wall 17. The front wall 17 has a pair of recesses 19 cut away inwardly so as extending downwardly, and spaced a distance on pitch equal to that between the concave portions 11 in the holder 10.

Figure 4:
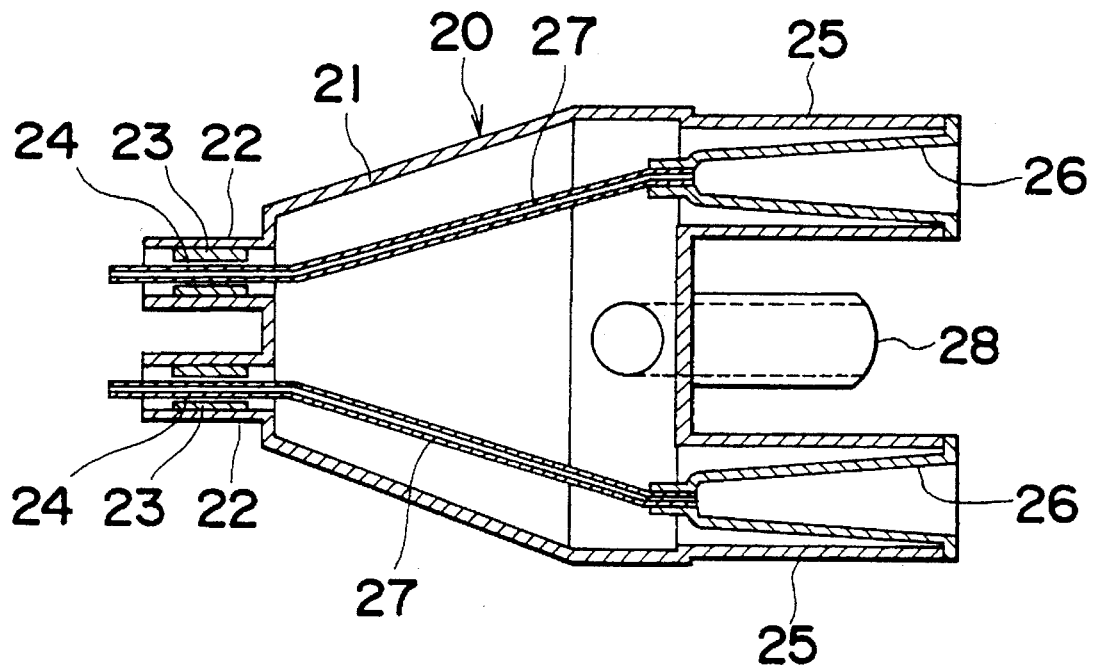
FIG. 4 is a top sectional view of a spray head shown in FIG. 1.
Figure 5:
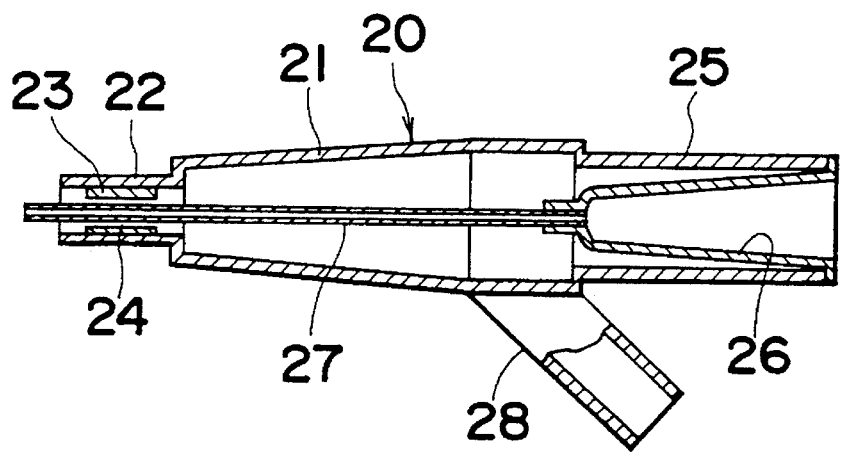
FIG. 5 is a side sectional view of the spray head.

A spray head 20 for spraying the fibrinogen and thrombin solutions discharged from the respective syringes 2 comprises, as shown in detail in FIGS. 4 and 5, a hollow housing 21 of a flattened truncated-pyramid or truncated-cone configuration. The housing 21 has at a front portion thereof a pair of parallel nozzles 22 for ejecting a sterile gas. Each nozzle 22 has its inner peripheral surface formed with a plurality of axial ribs 23 projecting radially inwardly therefrom so as to define a respective channel 24 surrounded by the axial ribs 23 for guiding an associated tube as will be described later.

The housing 21 also comprises at a rear end portion thereof a pair of cylindrical syringe connectors 25 to which respective nozzle adapters 26 having a generally conical configuration are inserted so that the syringe nozzles 5 will be fitted in from rear openings thereof. Each nozzle adapter 26 has an inner end fluid-coupled with one end of the associated tube 27 housed within the housing 21. Each tube 27 fluid-coupled with the nozzle adapter 26 extends through the associated channel 24 with its distal end protruding outwardly from the nozzle 22. Preferably, the length of the distal end of each tube 27 which protrudes outwardly from the nozzle 24 is chosen to be about 0.1 to 10 mm to ensure that the solutions ejected from the tubes 27 will be sprayed uniformly by the sterile gas emitted from the nozzles 22.

A bottom portion of the housing 21 has a gas supply tube 28 connected thereto so as to communicate with the interior of the housing 21. The gas supply tube 28 includes a sterilizing filter 29 (see FIG. 3) for sterilizing the gas fed from a pressurized gas source (not shown) before the gas is introduced into the housing 21. Generally, vinyl chloride tube is suited for the sterile gas supply tube. Preferably, the filter 29 is the form of MILLEX FG available from Millipore Corp. of U.S.A.

In assembling the applicator, for example, an amount of the fibrinogen solution is filled in one syringe 2, and an equal amount of the thrombin solution is accommodated in the other syringe 2. The syringes 2 are then fitted in the respective concave portions 11 of the holder 10, while the flanges 6 are inserted in the recesses, 15. The width of the uppermost opening of the recess 11 is set to be smaller than the external diameter of the barrel 3 so that the barrel 3 fitted is held tightly, which prevents the barrel 3 from moving or dropping therefrom. The thumb yoke 9 of the plungers 7 are inserted between the front and rear walls 17 and 18 of the actuator 16, and besides, the rear portions of the plungers 7 are engaged in the concave portions 19. The distance between the front and rear walls 17 and 18 is preferably so chosen as to be substantially equal to the thickness of thumb yokes 9. This ensures that the actuator 16 holds the plungers 7 without play.

Thereafter, the nozzles 5 of the barrels 3 are inserted into the adapters 26 in the spray head 20, respectively. The sterile gas supply tube 28 is connected to a tube (not shown) used to fluid-connected it with the pressurized gas source.

In operating the applicator 1, the sterile gas is fed from the sterile gas source through the sterile gas supply tube into the housing 21 and is then ejected from the nozzles 22. The solutions are ejected from the solution tube 27, by the application of an external push from the thumb finger of the user to the rear surface of the actuator 16 while the holder 10 and/or the flanges 6 is held between two fingers, i.e., fore- and middle-fingers. The solutions ejected from the tubes 27 are sprayed by the sterile gas ejected therearound, diffused and mixed together in the sterile gas, and are then applied to the surgical site. At that time, the solution tubes 27 are retained stably by the surrounding axial ribs 23, which keep the directions of the ejected solutions. This ensures that the solutions are applied exactly to the surgical site at which the nozzles are aimed.

Figure 6:
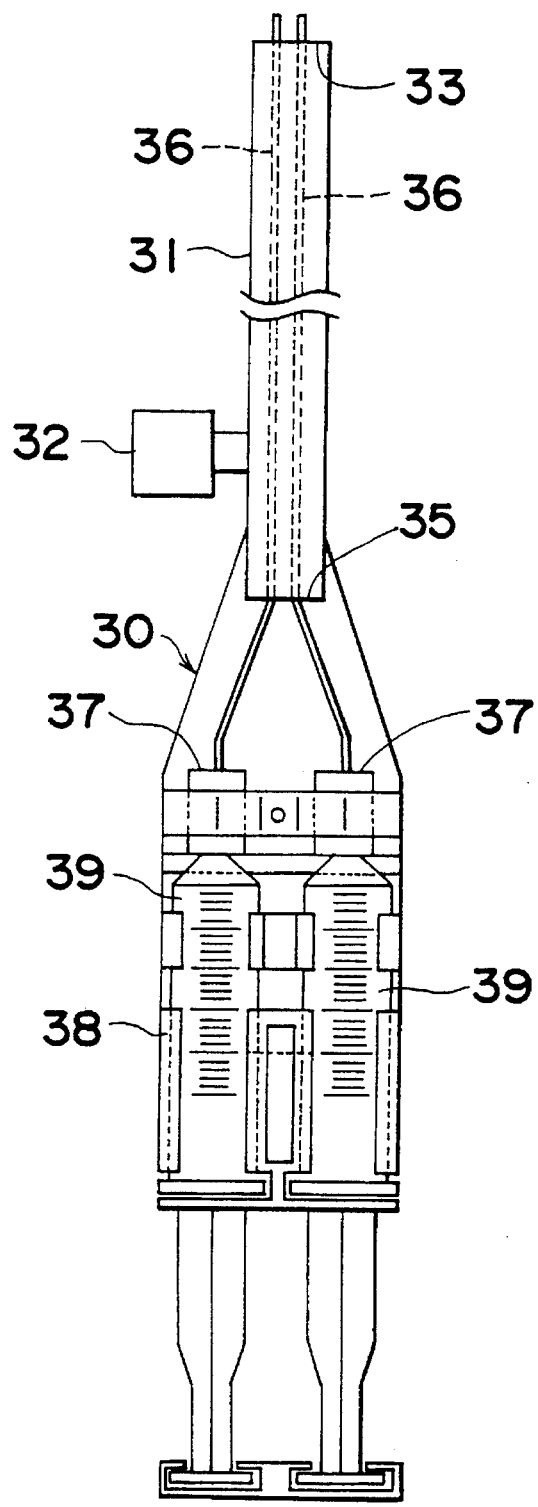
FIG. 6 is a plan view of the adhesive applicator in which an elongated tube is fitted to the spray head.
Figure 7:
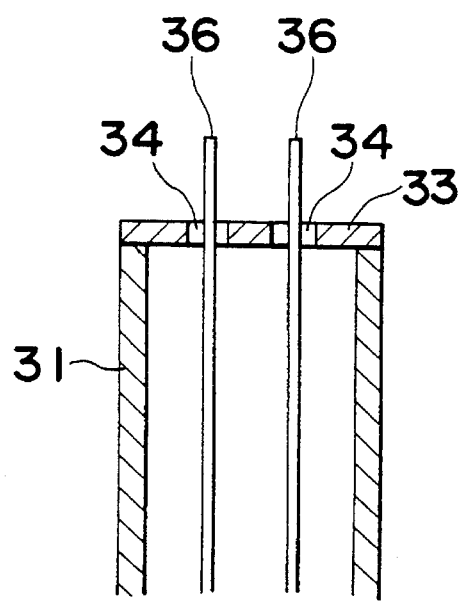
FIG. 7 is a partial cross sectional view, on an enlarged scale, of a distal end portion of the tube shown in FIG. 6.

FIG. 6 shows a modified form of the applicator. The applicator shown therein includes a spray head 30 having an elongated extension 31 of an approximate length of 5 to 50 cm so that the biocompatible adhesive can be applied to the surgical site which is relatively deep from the skin and visible to the naked eye or with an endoscope. The extension 31 is in the form of a hollow cylindrical pipe having a round or elliptic cross-section and closed at its opposite ends. This extension 31 has its interior fluid-connected with the sterile gas supply tube 32. As shown in FIG. 7, the tube 32 has a distal end 33 formed with a pair of through-holes or nozzles 34, through which respective solution tubes 36 extending into the extension 31 through a rear end plate 35 of such extension 31 are guided so as to protrude outwardly from the nozzles 34. A proximal end of each solution tube 35 which projects outwardly from the rear end plate 35 of the extension 31, there is connected a respective syringe nozzle adapter 37 for receiving the nozzles of the syringe 39 retained on the holder 38. Although it is not illustrated, each nozzle 34 preferably has its inner peripheral surface formed with a plurality of ribs projecting radially inwardly for supporting the associated solution tube 36 in coaxial relationship therewith.

Figure 8:
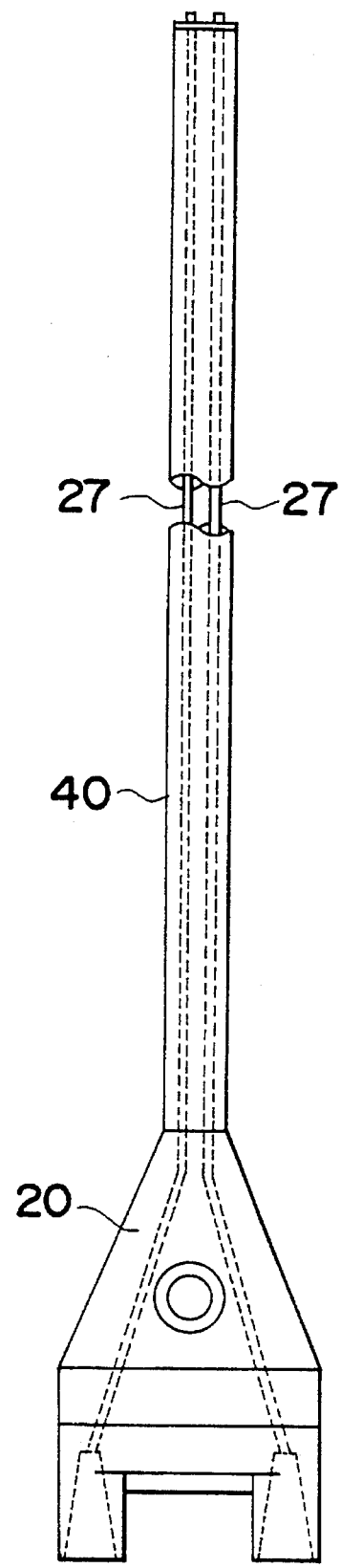
FIG. 8 is a plan view showing a modified form of the elongated tube fitted to the spray head.

In FIG. 8, there is shown the hollow spray head of the type shown in FIGS. 1 to 5, which incorporates an elongated hollow extension 40 at the distal end thereof. Using this type of spray head, it is possible to spray the adhesive to the deep surgical site treated by the use of a peritoneoscope.

Figure 9:
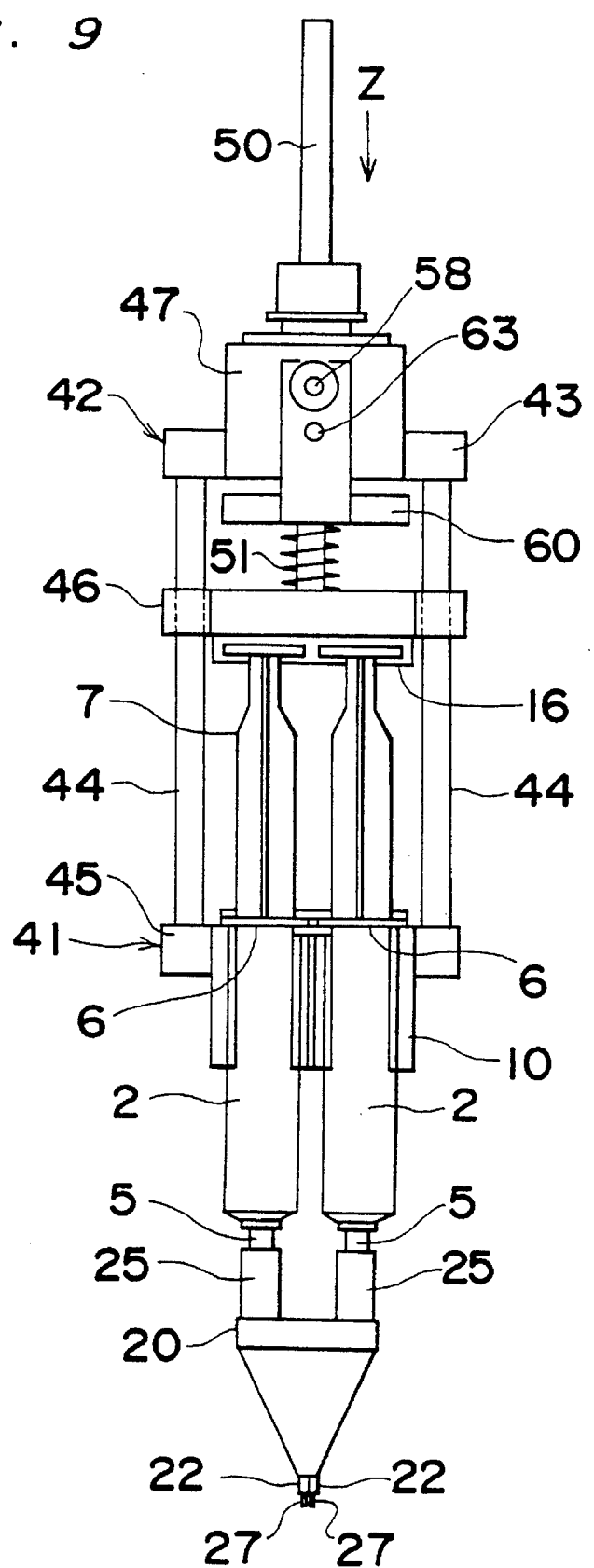
FIG. 9 is a plan view of the adhesive applicator according to another embodiment of the present invention.
Figure 10:
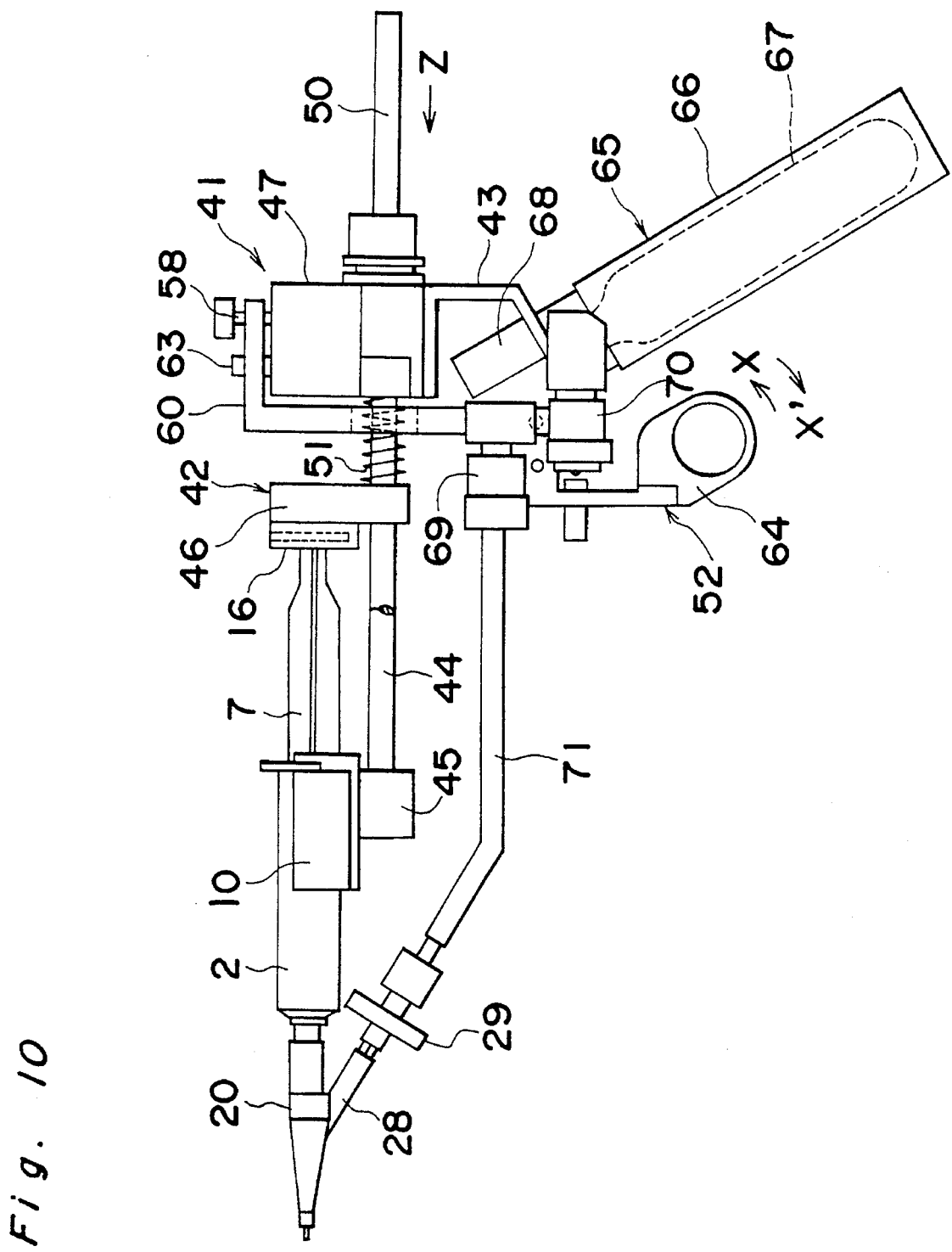
FIG. 10 is a side elevational view of the adhesive applicator shown in FIG. 9 with a guide rod removed.
Figure 11:
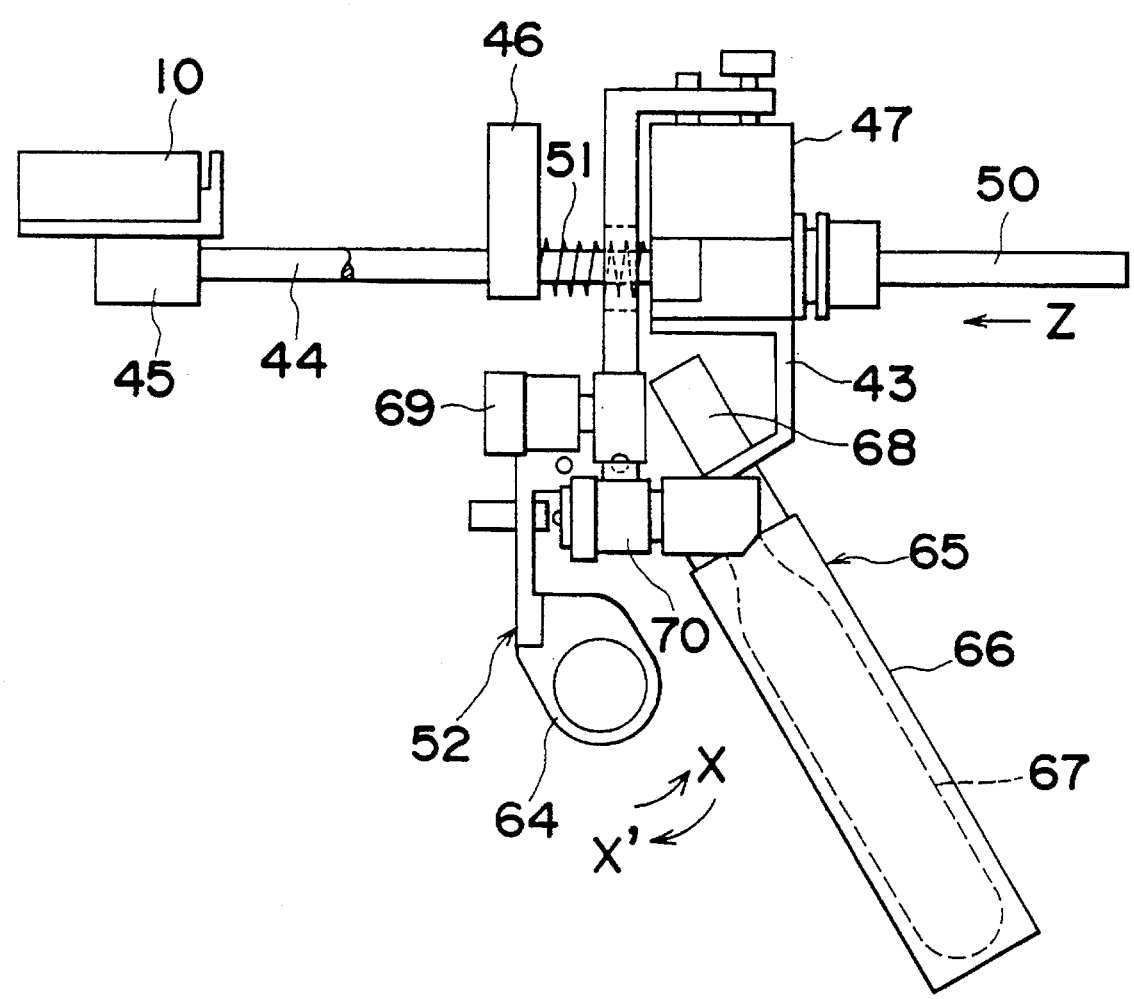
FIG. 11 is a side elevational view of the applicator shown in FIG. 9, in which the guide rod, syringes, spray head and sterile-gas supply tube are removed.

In FIGS. 9 and 10, there is shown another embodiment of the present invention in which a gun-type applicator for applying a biocompatible adhesive is generally shown by 41. This gun-type applicator 41 comprises, in addition to a holder 10 and an actuator 16, a feed mechanism 42 which supports the holder 10 and the actuator 16. This feed mechanism 42 automatically moves the actuator 16 towards the holder 10.

The feed mechanism 42 includes a frame 43 which is coupled to one ends of two parallel guide rods 44 spaced a predetermined distance therebetween. The other ends of the guide rods 44 are coupled to a connecting member 45 detachably carrying the holder 10. Axially slidably mounted on these guide rods 44 is a pushing member 46 which holds actuator 16 detachably.

The frame 43 has a braking box 47 mounted thereon. This braking box 47 has through-holes 48 and 49 defined in its forward and backward walls, respectively. Inserted in the through-holes 48 and 49 is a pressure rod 50 which extends parallel to the guide rods 44 and is fixed at its front end to the pushing member 46. Arranged between the braking box 47 and the pushing member 46 is a spring 51 operable to bias the pushing member 46 forwardly. An actual forward push of the pushing member 46 by the spring 51 takes place when a switching mechanism 52 described hereinafter is activated.

Figure 12:
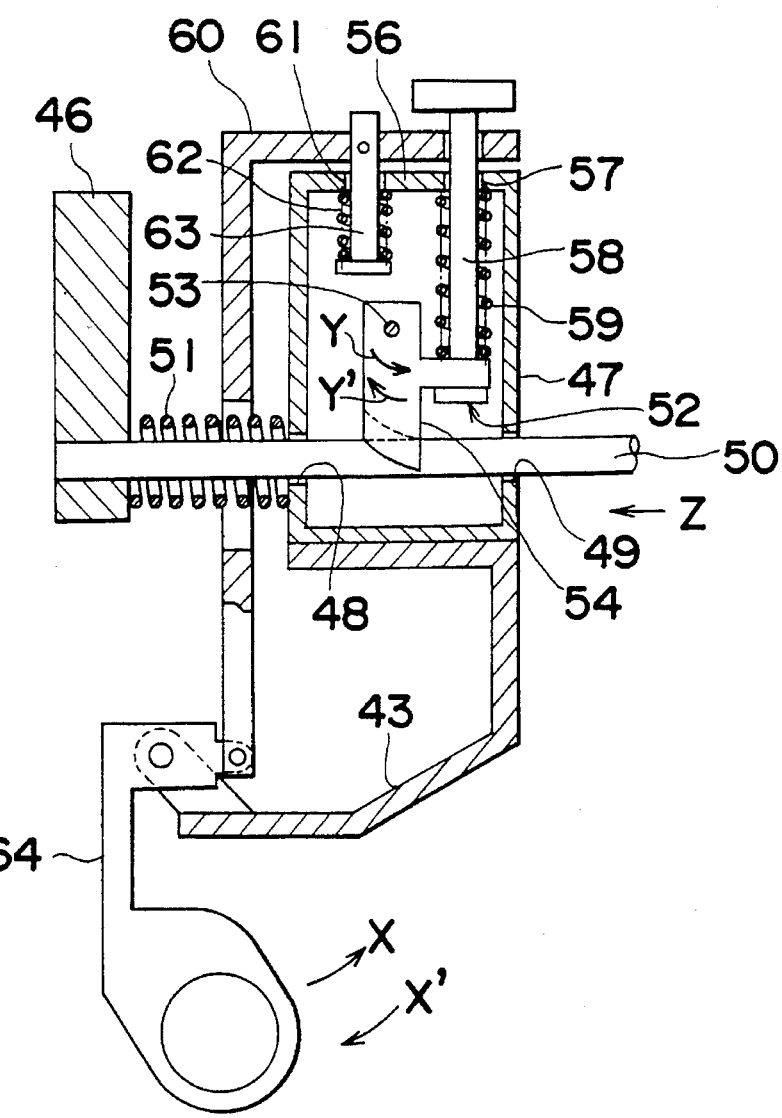
FIG. 12 is a sectional view, on an enlarged scale, of the adhesive applicator shown in FIG. 9.
Figure 13:
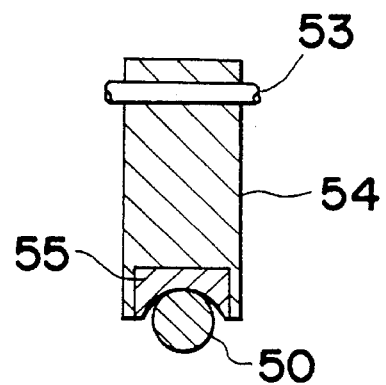
FIG. 13 is a sectional view of a pushing rod and a stopper brought into contact with each other.

As shown in detail in FIG. 12, the switching mechanism 52 comprises a braking member 54 disposed in the braking box 47. The braking member 54 is rotatably supported about a shaft 53 extending perpendicular to the pressure rod 50 and is provided with a friction member 55 frictionally engageable with the pressure rod 50 (see FIG. 13). Preferably, a surface area of the pressure rod 50 which is brought into contact with the friction member 55 is formed with surface irregularities so that a greater force of friction will be generated between the friction member 55 and the pressure rod 50. Rotatably coupled to the braking member 54 is a rod 58 extending through a through-hole 57 formed in the upper wall 56 of the braking box 47. This rod 58 carries on its periphery a helical spring 59 operable to bias the rod 58 so as to bring the friction member 55 into frictional contact with the pressure rod 50. Arranged above the upper and front surfaces of the braking box 47 is a connecting member 60 to which an end portion of the rod 58 protruding outwardly from the braking box 47 is engaged A rod 63 extending through a hole 61 defined in the upper wall 56 of the braking box 47 is connected to the connecting member 60. The rod 63 has a helical spring 62 mounted therearound so that the connecting member 60 is normally urged downward by the biasing force of the spring 62. Further, the connecting member 60 is rotatably coupled to a switching means, that is, a switching lever 64 rotatably supported on the frame 43. Therefore, upon moving the switching lever 64 in a direction indicated by the arrow X, the connecting member 60 is raised to rotate the braking member 54 in a direction indicated by the arrow Y, which permits the pressure rod 50 to move in a direction indicated by the arrow Z by the action of the biasing force of the spring 51. On the other hand, upon releasing the switching lever 64, by the action of the biasing force of the springs 59 and 62, the connecting member 60 descends so as to rotate the braking member 54 in a direction indicated by the arrow Y', which brings the pressure rod 50 to a halt.

The switching lever 64 has not only a function to control the movement of the pressure rod 50 in the direction indicated by the arrow Z, that is, the forward movement, as described before, but also another function to control the supply of the sterile gas from a sterile-gas supply unit 65 which will be discussed below.

The sterile gas supply unit 65 comprises a gas holder 66. This gas holder 66 is fixed to the frame 43 and serves as a grip for users. Therefore, in operation, the user holds the grip and engages his finger on the switching lever 64 to activate it. The gas holder 66 houses a miniature gas cylinder 67, the pressure of the gas ejected from the cylinder 67 being adjusted by a small-sized high-pressure regulator 68. An outlet of the gas cylinder 67 is connected to a connecting tube 69 so that gas accommodated in the gas cylinder 67 can be fed through the connecting tube 69 and another tube 71 connected thereto to the gas supply tube 28. The connecting tube 69 is incorporated with a valve 70 so that, upon moving the switching lever 64 in the direction indicated by arrow X, the valve 70 changes its position from a closed state to an opened state. For a gas cylinder 67, it is advantageous to use Mini Gas-Cartridge M-1509-EW-Cn2R available from NIPPON TANSAN GAS Co., LTD. Further, for the high pressure regulator 68, it is preferable to employ one, such as Gas Supply Unit NR-01 available from NIPPON TANSAN GAS Co., LTD., whose discharging pressure can be controlled within 0.5–4.0 kg/cm$^2$.

Operation of the gun-type applicator for automatically applying the biocompatible adhesive will be discussed below. Fibrinogen and thrombin solutions of the same amount are drawn into respective syringes 2. These syringes are fitted to the holder 10 while the thumb yokes 9 of the plungers 7 are housed in the actuator 16. Then, after moving the pressure rod 50 backward against the biasing force of the spring 51, the holder 10 is coupled to the connecting member 45 and, at the same time, the actuator 16 is coupled to the pushing member 46. Further, the spray head 20 is connected to the nozzles 5 of the syringes 2, while the sterile-gas supply tube 28 is connected through the extension tube 71 to the connecting tube 69.

In spraying the solution on the surgical site using the applicator thus prepared, the user grips the gas holder 66 with his forefinger engaged in the switching lever 64, directs the front nozzles 22 of the spray head 20 to the surgical site, and moves the switching lever 64 in the direction indicated by the arrow X. As a result, the valve 70 is changed from the closed position to the opened position according to the movement of the switching lever 64, such that the gas accommodated in the gas cylinder 67 is supplied through the connecting tube 69 and extension tube 71 to the filter 29, where it is sterilized, and is then ejected from the nozzle 22 through the housing 21 towards the surgical sites. Simultaneously, by the movement of the switching lever 64, the connecting member 60 and rods 58 and 63 move upward and the braking member 54 releases the rod 50 to move. Further, the pressure rod 50 moves forward, i.e., in the direction indicated by the arrow Z by the biasing force of the spring 51, and pushes the actuator 16 and plungers 7 through the pushing member 46. As a result, the solutions accommodated in the syringes 2 are ejected from the solution tubes 27, sprayed and mixed by the ejected sterile gas, and then applied onto the surgical site uniformly. Though, the sterile gas can be ejected simultaneously with the solutions, it is preferable to design the applicator that, upon moving the switching lever 64 in the direction indicated by arrow X, the sterile gas is ejected and then the solution is permitted to eject by the further movement of the switching lever 64 in the same direction.

Spraying of the solutions can be suspended only by releasing the switching lever 64. By this operation, the connecting member 60 moves downward, so that the braking member 50 presses the pressure rod 50 to prevent it from moving forward. Further, the switching lever 64 moves in a direction indicated by the arrow X' so that the valve changes from the opened position to the closed position, which eventually interrupts the supply of the gas from the gas cylinder 67. Accordingly, the amount of the solutions sprayed to the surgical site can readily be controlled by changing the position of the switching lever.

It is apparent from the above description that, since the gun-type applicator for applying the biocompatible adhesive incorporates the gas cylinder 67, it has advantages that transportation during the surgical operation can easily be done, the direction of spray of the adhesive can freely be changed, and a change between operating state and non-operating state can readily be done by one hand.

The invention being thus described, it will be obvious that the same may be varied within the scope of the appended claims.

What is claimed is:

1. An applicator useful for applying a biocompatible adhesive containing human or animal protein to a surgical site of a living body, comprising a spray head, a pair of syringes each including a barrel and a nozzle at one end of the barrel, the syringes adapted to feed a protein solution and a coagulation solution, wherein the nozzles are fitted into the spray head, wherein the spray head is adapted to spray the protein and coagulation solutions fed from the syringes by ejection of a sterile gas, wherein the spray head comprises a housing including a pair of adapters for receiving the nozzles of the syringes, a pair of adjacent sterile-gas ejecting nozzles in the housing, each having a longitudinal axes, wherein the longitudinal axis thereof are arranged for guiding and ejecting the sterile gas, and a pair of solution tubes, one arranged and associated within each sterile-gas ejecting nozzle, each having a longitudinal axes parallel to the longitudinal axes of the gas ejecting nozzles, wherein one end of each of the solution tubes is connected to one of the adapters, and the other end of each solution tube protrudes from the end of the associated sterile-gas ejecting nozzle, wherein the solution tubes are arranged such that when the solutions are fed from the syringes, they are conveyed through the solution tubes and ejected therefrom, and a sterile-gas supply tube connected to the interior of the housing adapted to supply the sterile gas.

2. An applicator according to claim 1, wherein each of the sterile-gas ejecting nozzles has its inner periphery surface formed with a plurality of ribs for supporting the associated solution tube in coaxial relationship therewith.

3. An applicator according to claim 1, wherein the distance between the pair of solution tubes is about 1 to 20 mm.

4. An applicator according to claim 1, wherein the distance between the pair of solution tubes is about 1 to 5 mm.

5. An applicator according to claim 1, wherein each solution tubes independently protrude outwardly from the associated sterile-gas ejection nozzles about 0.1 to 10 mm.

6. An applicator according to claim 1, wherein the spray head has an elongated hollow extension of about 5 to 50 cm, wherein the elongated hollow extension includes a pair of through holes through which the solution tubes outwardly protrude.

7. An applicator according to claim 6, wherein the sterile-gas supply tube is connected to the interior of the elongated hollow extension of about 5 to 50 cm.

8. An applicator according to claim 1, which further comprises a holder holding the pair of syringes.

9. An applicator according to claim 8, wherein the holder includes a pair of parallel concave portions adapted to receive the pair of syringes.

10. An applicator according to claim 1, which further comprises a pair of plungers inserted into the pair of syringe barrels.

11. An applicator according to claim 10, which further comprises an actuator holder holding and simultaneously moving the pair of plungers.

12. An applicator according to claim 1, which further comprises a pair of plungers adapted to be inserted into the pair of syringe barrels, a holder holding the pair of syringes, an actuator holding the pair of plungers, and a frame including a supporting member supporting the holder;

a pushing member for biasing and moving the actuator;

a sterile gas supply source for supplying the sterile gas; and switching means for controlling a supply of the sterile gas from the sterile gas supply source and for controlling movement of the pushing member.

13. An applicator according to claim 12, wherein the sterile gas supply source is a portable gas cylinder adapted to include the sterile gas therein.

14. An applicator according to claim 12, which is a gun-type applicator.

15. An applicator according to claim 1, wherein the sterile-gas supply tube includes a sterilizing filter adapted to sterilize the gas before the gas is introduced into the housing.

16. A spray head useful in an applicator for applying a biocompatible adhesive containing human or animal protein to a surgical site of a living body, comprising a housing including a pair of adapters for receiving nozzles of a syringe, a pair of adjacent sterile-gas ejecting nozzles in the housing, each having a longitudinal axes, wherein the longitudinal axis thereof are arranged for guiding and ejecting a sterile gas, and a pair of solution tubes, one arranged and associated within each sterile-gas ejecting nozzle, each having a longitudinal axes parallel to the longitudinal axes of the gas ejecting nozzles, wherein one end of each of the solution tubes is connected to one of the adapters, and the other end of each solution tube protrudes from the end of the associated sterile-gas ejecting nozzle, wherein the solution tubes are arranged such that when the solutions are fed from syringes, they are conveyed through the solution tubes and ejected therefrom, and a sterile-gas supply tube connected to the interior of the housing adapted to supply the sterile gas.

17. A spray head according to claim 16, wherein each of the sterile-gas ejecting nozzles has its inner periphery surface formed with a plurality of ribs for supporting the associated solution tube in coaxial relationship therewith.

18. A spray head according to claim 16, wherein the distance between the pair of solution tubes is about 1 to 20 mm.

19. A spray head according to claim 16, wherein the distance between the pair of solution tubes is about 1 to 5 mm.

20. A spray head according to claim 16, wherein each solution tubes independently protrude outwardly from the associated sterile-gas ejection nozzles about 0.1 to 10 mm.

21. A spray head according to claim 16, wherein the spray head has an elongated hollow extension of about 5 to 50 cm, wherein the elongated hollow extension includes a pair of through holes through which the solution tubes outwardly protrude.

* * * * *